(12) United States Patent
Miyazawa et al.

(10) Patent No.: US 11,390,808 B2
(45) Date of Patent: Jul. 19, 2022

(54) SINGLET OXYGEN SCAVENGER

(71) Applicant: SHISEIDO COMPANY, LTD., Tokyo (JP)

(72) Inventors: Kazuyuki Miyazawa, Yokohama (JP); Nozomi Fujiyama, Yokohama (JP); Azusa Kikuchi, Yokohama (JP); Mikio Yagi, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 134 days.

(21) Appl. No.: 16/625,227

(22) PCT Filed: Jun. 15, 2018

(86) PCT No.: PCT/JP2018/022920
§ 371 (c)(1),
(2) Date: Dec. 20, 2019

(87) PCT Pub. No.: WO2019/003963
PCT Pub. Date: Jan. 3, 2019

(65) Prior Publication Data
US 2020/0140754 A1  May 7, 2020

(30) Foreign Application Priority Data

Jun. 30, 2017  (JP) .............................. JP2017-128316

(51) Int. Cl.
| *C09K 15/20* | (2006.01) |
| *C09K 15/12* | (2006.01) |
| *C09K 15/06* | (2006.01) |
| *C09K 15/30* | (2006.01) |
| *A61K 31/216* | (2006.01) |
| *A61K 8/39* | (2006.01) |
| *A61K 8/49* | (2006.01) |
| *A61K 31/185* | (2006.01) |
| *A61K 8/58* | (2006.01) |
| *A61Q 17/04* | (2006.01) |
| *A61K 31/24* | (2006.01) |
| *A61K 31/277* | (2006.01) |
| *A61K 31/125* | (2006.01) |
| *A61P 39/06* | (2006.01) |
| *A61K 31/618* | (2006.01) |
| *A61K 31/4184* | (2006.01) |
| *A61K 31/53* | (2006.01) |
| *A61K 8/368* | (2006.01) |
| *A61K 31/80* | (2006.01) |

(52) U.S. Cl.
CPC .............. *C09K 15/20* (2013.01); *A61K 8/368* (2013.01); *A61K 8/39* (2013.01); *A61K 8/49* (2013.01); *A61K 8/58* (2013.01); *A61K 31/125* (2013.01); *A61K 31/185* (2013.01); *A61K 31/216* (2013.01); *A61K 31/24* (2013.01); *A61K 31/277* (2013.01); *A61K 31/4184* (2013.01); *A61K 31/53* (2013.01); *A61K 31/618* (2013.01); *A61K 31/80* (2013.01); *A61P 39/06* (2018.01); *A61Q 17/04* (2013.01); *C09K 15/06* (2013.01); *C09K 15/12* (2013.01); *C09K 15/30* (2013.01)

(58) Field of Classification Search
None
See application file for complete search history.

(56) References Cited

U.S. PATENT DOCUMENTS

| 5,723,435 | A  | * | 3/1998 | Severns  ............... | C11D 3/0084 |
| | | | | | 510/501 |
| 5,919,751 | A  | * | 7/1999 | Bird ........................ | C11D 3/33 |
| | | | | | 510/521 |
| 7,588,747 | B2 |   | 9/2009 | Naito et al. | |
| 8,426,490 | B2 | * | 4/2013 | Bissinger .............. | C07C 271/16 |
| | | | | | 523/117 |
| 9,096,882 | B2 |   | 8/2015 | Meyer et al. | |
| 2002/0094342 | A1 | * | 7/2002 | Wohlman ............... | A61Q 17/00 |
| | | | | | 424/401 |
| 2005/0008665 | A1 | * | 1/2005 | Batzer .................. | A61K 31/122 |
| | | | | | 424/401 |

(Continued)

FOREIGN PATENT DOCUMENTS

| CN | 101768403 | * | 7/2010 |
| JP | 10-121044 A |  | 5/1998 |

(Continued)

OTHER PUBLICATIONS

Bino et al., "Design, synthesis and biological evaluation of novel hydroxy-phenyl-1H-benzimidazoles as radical scavengers and UV-protective agents", Journal of Enzyme Inhibition and Medicinal Chemistry, Taylor & Francis, 2017, vol. 32, No. 1, pp. 527-537; Cited in EESR.
Extended European Search Report (EESR) dated Oct. 16, 2020 issued in the corresponding European Patent Application No. 18824021.2.
Virginie Lhiaubei -Vallet et al., "Filter-filter interactions. Photostabilization, triplet quenching and reactivity with singlet oxygen", Photochemical & Phobiological Sciences, 2010, pp. 552-558; Cited in ISR.
International Search Report (ISR) dated Sep. 25, 2018 filed in PCT/JP2018/022920 and a partial English translation.
International Search Opinion (PCT/ISA/237) dated Sep. 25, 2018 filed in PCT/JP2018/022920 and a partial English translation.

(Continued)

*Primary Examiner* — Tanisha Diggs
(74) *Attorney, Agent, or Firm* — Rankin, Hill & Clark LLP

(57) ABSTRACT

A singlet oxygen scavenger includes, as an active component, hexyl diethyl amino hydroxy benzoyl benzoate, 1-(4-methoxy phenyl)-3-(4-tert-butyl phenyl)-1, 3-propanedione, terephthalylidene-3, 3'-dicamphor-10, 10'-disulfonate, 2-ethyl hexyl 4-methoxy cinnamate, or 2-ethyl hexyl 2-cyano-3, 3-diphenyl acrylate; or 2-phenyl benzimidazole-5-sulfonic acid, 4, 4', 4"-[(1, 3, 5-triazine-2, 4, 6-triyl) tris (imino)] trisbenzoic acid tris (2-ethyl hexyl), octyl salicylate, or 3, 3, 5-trimethyl cyclohexyl salicylate; or 2-hydroxy-4-methoxy-5-(sodiooxysulfonyl) benzophenone, drometrizol trisiloxane, 2-hydroxy-4-methoxy benzophenone, or 4-methyl benzylidene camphor.

3 Claims, No Drawings

(56) References Cited

U.S. PATENT DOCUMENTS

| | | | |
|---|---|---|---|
| 2005/0129756 A1* | 6/2005 | Podhaisky | A61K 47/32 424/464 |
| 2010/0233110 A1 | 9/2010 | Cohen et al. | |
| 2012/0065307 A1* | 3/2012 | Cogen | C08L 75/04 524/127 |
| 2012/0141394 A1 | 6/2012 | Chaudhuri | |
| 2012/0141395 A1 | 6/2012 | Chaudhuri | |
| 2017/0044340 A1 | 2/2017 | Farah et al. | |
| 2017/0135920 A1* | 5/2017 | Enomoto | A61Q 1/02 |

FOREIGN PATENT DOCUMENTS

| | | | |
|---|---|---|---|
| JP | 2001-122765 A | | 5/2001 |
| JP | 2003-26560 A | | 1/2003 |
| JP | 2005336115 | * | 12/2005 |
| JP | 4763460 B2 | | 6/2011 |
| JP | 2013-173681 A | | 9/2013 |
| JP | 5770428 B2 | | 8/2015 |
| JP | 5883226 B2 | | 3/2016 |

OTHER PUBLICATIONS

Chinese Office Action (CNOA) dated May 17, 2022 issued in the corresponding Chinese patent application No. 201880041340.5.
A. Bino et al., "Design, synthesis and biological evaluation of novel hydroxy-phenyl-1H-benzimidazoles as radical scavengers and UV-protective agents", Journal of Enzyme Inhibition and Medicinal Chemistry, vol. 32, No. 1, pp. 527-537, 2017; Cited in CNOA.

* cited by examiner

SINGLET OXYGEN SCAVENGER

CROSS-REFERENCE TO RELATED APPLICATIONS

This application is a National Phase Entry of PCT International Application No. PCT/JP2018/022920 filed on Jun. 15, 2018, which claims priority under 35 U.S.C § 119(a) to Japanese Patent Application No. 2017-128316 filed on Jun. 30, 2017. Each of the above applications is hereby expressly incorporated by reference, in its entirety, into the present application.

TECHNICAL FIELD

The present disclosure relates to a singlet oxygen scavenger.

BACKGROUND ART

Humans live by utilizing oxygen, but some oxygen is active oxygen, and this active oxygen is known to cause various diseases and aging. Active oxygen species generated by ultraviolet rays are also recognized as causing skin damage and premature aging. Substances that exhibit the action of eliminating the active oxygen species are also known. For example, benzophenone derivatives derived from Hypericaceae plants (Japanese Unexamined Patent Publication No. H10-121044), flavonoids and tannins derived from plant extracts (Japanese Unexamined Patent Publication No. 2003-26560), various plant extracts, and 2-hydroxy-4-methylbenzophenone-5-sulfate (Japanese Unexamined Patent Publication No. 2001-122765), and the like are known as substances that have radical scavenging activity.

Incidentally, active oxygen species are roughly classified into radical types and non radical types. Hydroxy radicals (.OH), alkoxy radicals (LO.), peroxy radicals (LOO.), hydroperoxy radicals (HOO.), nitric oxide (NO.), nitrogen dioxide ($NO_2$.), superoxide ($O_2^-$.), etc. are radical types of active oxygen, in descending order of reactivity. Non-radicals include singlet oxygen ($^1O_2$), ozone ($O_3$), hydrogen peroxide ($H_2O_2$), lipid hydroperoxide (LOON), etc. That is, what have been conventionally referred to as active oxygen species include those which are radical and non radical, and there are reducing molecular species in which the number of electrons is different from that of ground state oxygen, such as superoxide, hydroxy radical, and hydrogenated hydrogen peroxide. In addition, there is singlet oxygen, which is an excited molecular species that has the same number of electrons as the ground state oxygen but is in an excited state. These species have unique properties according to a narrow definition, based on the differences in the states of electrons therein.

Among active oxygen species, superoxide and hydroxy radicals, for example, react with proteins and readily cause fragmentation, but singlet oxygen forms crosslinks to proteins and polymerizes proteins, and exhibits a unique reactivity which is completely different from such radical active oxygen species such as superoxide etc. In addition, because singlet oxygen has a denaturing action on protein, it has also become clear that singlet oxygen causes peroxidation of sebum which causes various skin troubles. However, as described above, active oxygen species have unique characteristics depending on the types thereof. For example, it cannot be predicted whether a radical active oxygen scavenger such as that which is disclosed in Japanese Unexamined Patent Publication No. 2001-122765 will function as a singlet oxygen scavenger.

From these viewpoints, studies specializing in singlet oxygen scavengers in particular have also been conducted. For example, Japanese Patent No. 4763460 discloses a colloid of platinum or rhodium that contains polyvinylpyrrolidone, Japanese Patent No. 5770428 discloses a rosemary extract, Japanese Patent No. 5883226 discloses a humus soil extract, and Japanese Unexamined Patent Publication No. 2013-173681 discloses an aloe juice as a singlet oxygen scavenger, respectively.

SUMMARY

Technical Problem

However, substances which are known as singlet scavengers have poor chemical stability. Therefore, they deteriorate during storage over time, and the singlet oxygen scavenging function of many of them decrease. Accordingly, there is demand for improvements in the persistence of singlet oxygen scavenging effect.

The present disclosure has been developed in view of the foregoing circumstances. The present disclosure provides a singlet oxygen scavenger having a high signet oxygen scavenging function.

A first singlet oxygen scavenger of the present disclosure has hexyl diethyl amino hydroxy benzoyl benzoate, 1-(4-methoxy phenyl)-3-(4-tert-butyl phenyl)-1,3-propanedione, terephthalylidene-3, 3'-dicamphor-10, 10'-disulfonate, 2-ethyl hexyl 4-methoxy cinnamate, or 2-ethyl hexyl 2-cyano-3, 3-diphenyl acrylate as an active component.

A second singlet oxygen scavenger of the present disclosure has 2-phenyl benzimidazole-5-sulfonic acid, 4,4',4"-[(1,3,5-triazine-2,4,6-triyl) tris (imino)] trisbenzoic acid tris (2-ethyl hexyl), octyl salicylate, or 3,3,5-trimethyl cyclohexyl salicylate as an active component.

A third singlet oxygen scavenger of the present disclosure has 2-hydroxy-4-methoxy-5-(sodiooxysulfonyl) benzophenone, drometrizol trisiloxane, 2-hydroxy-4-methoxy benzophenone, or 4-methyl benzylidene camphor as an active component.

The singlet oxygen scavenger of the present disclosure has a high singlet oxygen scavenging function. Therefore, the singlet oxygen scavenger of the present disclosure may be utilized to suppress various reactions that singlet oxygen is involved in.

DESCRIPTION OF EMBODIMENTS

The singlet oxygen scavenger of the present disclosure will be described in detail below.

A first singlet oxygen scavenger of the present disclosure has hexyl diethyl amino hydroxy benzoyl benzoate, 1-(4-methoxy phenyl)-3-(4-tert-butyl phenyl)-1, 3-propanedione, terephthalylidene-3, 3'-dicamphor-10, 10'-disulfonate, 2-ethyl hexyl 4-methoxy cinnamate, or 2-ethyl hexyl 2-cyano-3, 3-diphenyl acrylate as an active component.

The CAS Number of hexyl diethyl amino hydroxy benzoyl benzoate is 302776-68-7. Hexyl diethyl amino hydroxy benzoyl benzoate is commercially available as Uvinul A Plus from BASF.

The CAS Number of 1-(4-methoxy phenyl)-3-(4-tert-butyl phenyl)-1, 3-propanedione is 70356-09-01, and 1-(4-methoxy phenyl)-3-(4-tert-butyl phenyl)-1, 3-propanedione is commercially available as Parsol 1789 from DSM.

The CAS Number of terephthalylidene-3, 3'-dicamphor-10, 10'-disulfonate is 92761-26-7, and terephthalylidene-3, 3'-dicamphor-10, 10'-disulfonate is commercially available as Mexoryl SX from CHIMEX, and also as Ecamsule from SIGMA-ALDRICH.

The CAS Number of 2-ethyl hexyl 4-methoxy cinnamate is 5466-77-3, and 2-ethyl hexyl 4-methoxy cinnamate is commercially available as Parsol MCX from DSM and as Uvinul MC80 from BASF.

The CAS Number of 2-ethyl hexyl 2-cyano-3, 3-diphenyl acrylate is 6197-30-4, and 2-ethyl hexyl 2-cyano-3, 3-diphenyl acrylate is commercially available as Parsol 340 from DSM, Uvinul N539T from BASF, and as Eusolex OCR from MERCK.

A second singlet oxygen scavenger of the present disclosure has 2-phenyl benzimidazole-5-sulfonic acid, 4,4',4"-[(1,3,5-triazine-2,4,6-triyl) tris (imino)] trisbenzoic acid tris (2-ethyl hexyl), octyl salicylate, or 3,3,5-trimethyl cyclohexyl salicylate as an active component.

The CAS Number of 2-phenyl benzimidazole-5-sulfonic acid is 27503-81-7, and 2-phenyl benzimidazole-5-sulfonic acid is available as Eusolex 232 from MERCK and as Parsol HS from DSM.

4,4',4"-[(1,3,5-triazine-2,4,6-triyl) tris (imino)] trisbenzoic acid tris (2-ethyl hexyl) is also referred to as 2,4,6-tris [4-(2-ethyl hexyl oxycarbonyl) anilino]-1,3,5-triazine), and the CAS Number thereof is 88122-99-0. 4,4',4"-[(1,3,5-triazine-2,4,6-triyl) tris (imino)] trisbenzoic acid tris (2-ethyl hexyl) is commercially available as Uvinul T150 from BASF.

The CAS Number of octyl salicylate is 118-60-5, and octyl salicylate is commercially available as Neoheliopan OS from SYMRISE. The CAS Number of 3,3,5-trimethyl cyclohexyl salicylate is 118-56-9, and 3,3,5-trimethyl cyclohexyl salicylate is commercially available as Neoheliopan HMS from SYMRISE.

A third singlet oxygen scavenger of the present disclosure has 2-hydroxy-4-methoxy-5-(sodiooxysulfonyl) benzophenone, drometrizol trisiloxane, 2-hydroxy-4-methoxy benzophenone, or 4-methyl benzylidene camphor as an active component.

The CAS Number of 2-hydroxy-4-methoxy-5-(sodiooxysulfonyl) benzophenone is 6628-37-1, and 2-hydroxy-4-methoxy-5-(sodiooxysulfonyl) benzophenone is commercially available as Uvinul MS40 from BASF.

The CAS Number of drometrizol trisiloxane is 155633-54-8, and drometrizol trisiloxane is commercially available as drometrizole trisiloxane from SIGMA-ALDRICH.

2-hydroxy-4-methoxy benzophenone is also referred to as benzophenone 3, and the CAS Number thereof is 131-57-7. 2-hydroxy-4-methoxy benzophenone is commercially available from BASF.

The CAS Number of 4-methyl benzylidene camphor is 36861-47-9, and 4-methyl benzylidene camphor is available as Parsol MBC from DSM.

It is possible to evaluate the singlet oxygen scavenging function of the singlet oxygen scavenger of the present disclosure by a singlet oxygen quenching rate constant. In the Stern-Volmer equation below, kQ is a singlet oxygen quenching rate constant, [Q] is a concentration of the singlet oxygen scavenger, $\tau_0$ is the lifetime of singlet oxygen a solution to which the singlet oxygen scavenger is not added, and $\tau$ is the lifetime of singlet oxygen a solution to which the singlet oxygen scavenger is added.

$$\tau_0/\tau = 1 + \tau_0 \cdot kQ \cdot [Q]$$

A line is obtained by plotting $\tau/\tau_0$ against [Q] (Stern-Volmer plot), and kQ can be derived from the slope of the line and the value of $\tau_0$. Note that in equations and experiments in which $\tau/\tau_0$ indicates an effect, $\tau_0/\tau$ is utilized to obtain the rate constant.

The singlet oxygen scavenger of the present disclosure may be blended with pharmaceuticals, cosmetics (including medicinal cosmetics), supplements, foods and the like alone, or in combination with one or more known additives according to conventional methods. Because singlet oxygen is abundant on the skin surface, which is constantly in contact with oxygen and exposed to ultraviolet rays, the singlet oxygen scavenger of the present disclosure is more useful in applications as an external preparation for skin. In addition, the reactions which are suppressed by the elimination of singlet oxygen are reactions that contribute to skin aging, skin darkening, and skin damage, and thus the singlet oxygen scavenger of the present disclosure which is capable of suppressing such reactions is particularly useful as a skin cosmetic for the purpose of preventing skin aging, whitening and skin beautification.

The amount of the singlet oxygen scavenger of the present disclosure to be blended differs depending on the singlet oxygen scavenger ability of the singlet oxygen scavenger in addition to the form of dosage, the intended purpose of use, etc. Generally, it is preferable for the content of the singlet oxygen scavenger to be within a range from 0.01 to 20% by mass, and more preferably 0.1 to 10% by mass of an ultimate composition. Within this range, the singlet oxygen scavenger will be capable of being blended stably, and a superior singlet oxygen scavenging function will be capable of being exhibited.

The form of the singlet oxygen scavenger of the present disclosure may be selected as appropriate according to the intended purpose, and the singlet oxygen scavenger may be a liquid or a dried solid. The solid may be a solid or a powder. In the case that the singlet oxygen scavenger is a solid, the solid may be dissolved or dispersed in a suitable liquid, or mixed with or adsorbed to a suitable powder carrier. In some cases, an emulsifying agent, a dispersing agent, a suspending agent, a spreading agent, a permeating agent, a moisturizing agent, a stabilizing agent, etc. may be added, and the singlet oxygen scavenger may be utilized in a preparation such as an emulsified agent, an oil based agent, a wettable powder agent, a powder agent, a tablet, a capsule, and a liquid.

In the case that the singlet oxygen scavenger is utilized in an external preparation for the skin and a cosmetic, it may be in the form of a liquid, a gel, a cream, a semisolid, a solid, a stick, a powder, etc. The singlet oxygen scavenger may be utilized in an emulsion, a cream, a lotion, a cosmetic liquid, a facial pack, a facial cleanser, a makeup cosmetic, a hair cosmetic, etc.

EXAMPLES

The singlet oxygen quenching function of the singlet oxygen scavenger of the present disclosure was evaluated by measuring a singlet oxygen quenching rate constant kQ by the following procedure.

<Measuring Devices>
(1) Detector
Near Infrared Photomultiplier Tube Module by HAMAMATSU PHOTONICS
Model: H10330A-45, Wavelength Range: 950 to 1400 nm
(2) Spectrometer
Miniature Spectrometer by SHIMADZU
Model: SPG-120IR, Wavelength Range: 700 to 2500 nm
(3) Light Source
Nd:YAG Laser, Continuum (CONTINUUM, USA)
Model: Surelite I, Wavelength Range: 1064, 532, 355, and 266 nm
(4) Data Processor
Digital Oscilloscope, Tektronix (TEKTRONIX, USA)
Model: TDS 3012C, Frequency Band: 100 MHz <Measurement Procedure>
(Preparation of Samples)

Rose Bengal (RB), which is a red pigment, was dissolved in a solvent (selected as appropriate from among acetonitrile, acetone, and heavy water according to favorable solubility) as a photosensitizer for generating singlet oxygen. The concentration of RB was set such that the absorbance at 532 nm was within an approximate range from 0.4 to 0.5. The RB solution was dissolved in a solvent so that each of the singlet oxygen scavengers shown in Table 1 was of a predetermined concentration, and the solution was prepared and subjected to the following measurement. In addition, the substances shown in Table 2 were prepared in a similar manner and subjected to the following measurement.
(Measurement)

RB was excited employing 532 nm light from the Nd: YAG laser (a structure in which yttrium, aluminum, and garnet single crystals are doped with $Nd^{+3}$ ions), and singlet oxygen was generated by energy transfer from RB to oxygen molecules. Only RB absorbs light at 532 nm, and the singlet oxygen scavengers do not. The light emitted from the solutions that contain the singlet oxygen scavengers was dispersed by the miniature spectrometer. 1274 nm near infrared phosphorescence, which is specific to singlet oxygen, was detected with the near infrared photomultiplier tube module and recorded on the digital oscilloscope. The attenuation curve of the near infrared phosphorescence emitted by the singlet oxygen was analyzed, and the lifetime $\tau$ of singlet oxygen at each concentration of the added singlet oxygen scavenger was obtained. In addition, the lifetime $\tau 0$ of singlet oxygen was determined in a solution to which no singlet oxygen scavenger was added (a solution with no added singlet oxygen scavenger).

The singlet oxygen quenching rate constant $kQ$ was calculated by the aforementioned Stern-Volmer equation for each concentration $[Q]$ of the singlet oxygen scavenger, the lifetime $\tau 0$ without the addition of the singlet oxygen scavenger, and the lifetime $\tau$ of singlet oxygen in the solutions to which singlet oxygen scavengers were added. Table 1 shows the results which were obtained.

The larger the singlet oxygen quenching rate constant $kQ$, the greater the singlet oxygen scavenging function.

TABLE 1

| | Substance Name and CAS Number | Concentration | $\tau/\tau_0$ | Singlet Oxygen Quenching Rate Constant kQ (Solvent) |
|---|---|---|---|---|
| 1 | 2-phenyl benzimidazole-5-sulfonic acid<br>2-phenyl benzimidazole-5-sulfonic acid<br>27503-81-7 | 3% | $\tau/\tau_0 = 1/28$<br>($\tau_0 = 64$ μs) | $3.5 \times 10^6$<br>($D_2O$—NaOH) |
| 2 | hexyl diethyl amino hydroxy benzoyl benzoate<br>n-hexyl 2-(4-diethylamino-2-hydroxybenzoyl)benzoate<br>302776-68-7 | 10% | $\tau/\tau_0 = 1/6.0$<br>($\tau_0 = 73$ μs) | $3.5 \times 10^5$<br>(Acetonitrile) |
| 3 | 2-hydroxy-4-methoxy-5-(sodiooxysulfonyl) benzophenone<br>sodium 2-hydroxy-4-methoxybenzophenone-5-sulfonate<br>6628-37-1 | 10% | $\tau/\tau_0 = 1/5.1$<br>($\tau_0 = 68$ μs) | $2.0 \times 10^5$<br>($D_2O$) |
| 4 | Drometrizole trisiloxane<br>2-(2H-benzotriazol-2-yl)-4-methyl-6-[2-methyl-3-[1,3,3,3-tetramethyl-1-[(trimethylsilyl)oxy]disiloxany]propyl] phenol<br>155633-54-8 | 15% | $\tau/\tau_0 = 1/1.9$<br>($\tau_0 = 54$ μs) | $7.3 \times 10^4$<br>(Acetone) |
| 5 | 1-(4-methoxy phenyl)-3-(4-tert-butyl phenyl)-1,3-propanedione 4-tert-butyl-4'-methoxydibenzoylmethane<br>70356-09-1 | 10% | $\tau/\tau_0 = 1/1.7$<br>($\tau_0 = 73$ μs) | $4.0 \times 10^4$<br>(Acetonitrile) |
| 6 | terephthalylidene-3,3'-dicamphor-10,10'-disulfonate<br>terephthalylidene-3,3'-dicamphor-10,10'-disulfonic acid<br>92761-26-7 | 10% | $\tau/\tau_0 = 1/1.4$<br>($\tau_0 = 68$ μs) | $3.6 \times 10^4$<br>($D_2O$—KOH) |
| 7 | 2-ethyl hexyl 4-methoxy cinnamate<br>2-ethylhexyl 4-methoxycinnamate<br>5466-77-3 | 20% | $\tau/\tau_0 = 1/1.6$<br>($\tau_0 = 73$ μs) | $1.4 \times 10^4$<br>(Acetonitrile) |
| 8 | 2-ethyl hexyl 2-cyano-3,3-diphenyl acrylate<br>2-ethylhexyl 2-cyano-3,3-diphenylacrylate<br>6197-30-4 | 10% | $\tau/\tau_0 = 1/1.2$<br>($\tau_0 = 73$ μs) | $1.2 \times 10^4$<br>(Acetonitrile) |
| 9 | 2-hydroxy-4-methoxy benzophenone<br>2-hydroxy-4-methoxybenzophenone<br>131-57-7 | 5% | $\tau/\tau_0 = 1/1.1$<br>($\tau_0 = 73$ μs) | $0.96 \times 10^4$<br>(Acetonitrile) |
| 10 | Octyl salicylate<br>2-ethylhexyl salicylate<br>118-60-5 | 10% | $\tau/\tau_0 = 1/1.2$<br>($\tau_0 = 73$ μs) | $8.0 \times 10^3$<br>(Acetonitrile) |
| 11 | 4-methyl benzylidene camphor<br>4-methylbenzylidenecamphor<br>36861-47-9 | 4% | $\tau/\tau_0 = 1/1.04$<br>($\tau_0 = 73$ μs) | $4.3 \times 10^3$<br>(Acetonitrile) |
| 12 | 3,3,5-trimethyl cyclohexyl salicylate<br>3,3,5-trimethylcyclohexyl salicylate<br>118-56-9 | 10% | $\tau/\tau_0 = 1/1.20$<br>($\tau_0 = 73$ μs) | $9.2 \times 10^3$<br>(Acetonitrile) |
| 13 | 4,4',4''-[(1,3,5-triazine-2,4, 6-triyl) tris (imino)] trisbenzoic acid tris (2-ethyl hexyl)<br>2,4,6-tris[4-(2-ethylhexyloxycarbonyl)-anilino]-1,3,5-triazine<br>88122-99-0 | 5% | $\tau/\tau_0 = 1/1.09$<br>($\tau_0 = 54$ μs) | $3.5 \times 10^4$<br>(Acetone) |

As is clear from Table 1 and Table 2 below, it can be understood that the singlet oxygen scavenger of the present disclosure has a high singlet oxygen scavenging function.

TABLE 2

| | Substance Name and CAS Number | Concentration | $\tau/\tau_0$ | Singlet Oxygen Quenching Rate Constant kQ (Solvent) |
|---|---|---|---|---|
| 14 | Bis(2-ethyl hexyl)= naphthalene-2,6-dicarboxylate diethylhexyl 2,6-napthalate 127474-91-3 | 10% | $\tau/\tau_0 > 1/1.02$ ($\tau_0 = 14$ μs) | Rate Constant not obtained Cmax = 0.2 mol dm$^{-3}$ (Acetonitrile) |

The invention claimed is:

1. A method of scavenging singlet oxygen, comprising contacting singlet oxygen with one selected from a group consisting of:

1-(4-methoxy phenyl)-3-(4-tert-butyl phenyl)-1,3-propanedione; and terephthalylidene-3,3'-dicamphor-10,10'-disulfonate.

2. A method of scavenging singlet oxygen, comprising contacting singlet oxygen with one selected from a group consisting of:

2-phenyl benzimidazole-5-sulfonic acid;

4, 4', 4"-[(1, 3, 5-triazine-2, 4, 6-triyl) tris (imino)] tris-benzoic acid tris (2-ethyl hexyl);

octyl salicylate; and 3, 3, 5-trimethyl cyclohexyl salicylate.

3. A method of scavenging singlet oxygen, comprising contacting singlet oxygen with one selected from a group consisting of:

2-hydroxy-4-methoxy-5-(sodiooxysulfonyl) benzophenone;

drometrizole trisiloxane; and 4-methyl benzylidene camphor.

* * * * *